(12) United States Patent
Coon et al.

(10) Patent No.: US 11,654,399 B2
(45) Date of Patent: May 23, 2023

(54) METHOD FOR MICROMOLDING A POLYMERIC MEMBRANE HAVING A PORE ARRAY

(71) Applicant: President and Fellows of Harvard College, Cambridge, MA (US)

(72) Inventors: David James Coon, Cambridge, MA (US); Tiama Hamkins-Indik, Cambridge, MA (US); Donald E. Ingber, Boston, MA (US); Miles Ingram, Cambridge, MA (US); Daniel Levner, Brookline, MA (US); Richard Novak, Jamaica Plain, MA (US); Jefferson Puerta, Malden, MA (US); Daniel E. Shea, Mendon, MA (US); Josiah Sliz, Boston, MA (US); Norman Wen, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 274 days.

(21) Appl. No.: 15/558,191

(22) PCT Filed: Mar. 16, 2016

(86) PCT No.: PCT/US2016/022680
§ 371 (c)(1),
(2) Date: Sep. 13, 2017

(87) PCT Pub. No.: WO2016/149394
PCT Pub. Date: Sep. 22, 2016

(65) Prior Publication Data
US 2018/0071690 A1    Mar. 15, 2018

Related U.S. Application Data

(60) Provisional application No. 62/134,550, filed on Mar. 17, 2015.

(51) Int. Cl.
*B01D 67/00* (2006.01)
*B29C 41/38* (2006.01)
(Continued)

(52) U.S. Cl.
CPC ......... *B01D 67/0034* (2013.01); *B01D 71/70* (2013.01); *B01L 3/502707* (2013.01);
(Continued)

(58) Field of Classification Search
CPC .... B01D 67/0034; B01D 71/70; C12M 25/02; B29C 39/26; B29C 33/424; B29C 41/36;
(Continued)

(56) References Cited

U.S. PATENT DOCUMENTS

| 2,523,410 A | | 9/1950 | Allard | |
| 3,649,456 A | * | 3/1972 | Benneville et al. | C12N 9/00 530/844 |

(Continued)

FOREIGN PATENT DOCUMENTS

| AU | 2012340576 A1 | * | 4/2015 | ............. A61P 35/04 |
| CA | 2811651 A1 | * | 4/2012 | ............. B01D 69/02 |

(Continued)

OTHER PUBLICATIONS

Porosity Science Direct NPL (Year: 2022).*

(Continued)

*Primary Examiner* — Xiao S Zhao
*Assistant Examiner* — Guy F Mongelli
(74) *Attorney, Agent, or Firm* — Nixon Peabody LLP

(57) ABSTRACT

A method for micro-molding a polymeric membrane and including pouring a predetermined volume of curable polymer unto a micro-fabricated mold having a post array with pillars, and overlaying the polymer with a support substrate. A spacer, such as a rubber spacer, is placed in contact with the support substrate and a force is applied to an exposed (Continued)

side of the spacer to compress the support substrate and the polymer together. While applying the force, the polymer is cured on the mold for a predetermined time period and at a predetermined temperature to form a polymeric membrane having a pore array with a plurality of pores corresponding to the plurality of pillars of the post array. The polymeric membrane is removed from the support substrate.

13 Claims, 6 Drawing Sheets

(51) Int. Cl.
  B29C 33/42    (2006.01)
  B29C 33/68    (2006.01)
  B29C 39/00    (2006.01)
  B29C 39/26    (2006.01)
  B29C 41/12    (2006.01)
  B01L 3/00     (2006.01)
  B29C 41/36    (2006.01)
  B01D 71/70    (2006.01)
  C12M 1/12     (2006.01)
  B29L 31/00    (2006.01)
  B29C 43/02    (2006.01)

(52) U.S. Cl.
  CPC ............ B29C 33/424 (2013.01); B29C 33/68 (2013.01); B29C 39/006 (2013.01); B29C 39/26 (2013.01); B29C 41/12 (2013.01); B29C 41/36 (2013.01); B29C 41/38 (2013.01); C12M 25/02 (2013.01); B01L 2300/123 (2013.01); B01L 2400/086 (2013.01); B29C 2043/025 (2013.01); B29L 2031/755 (2013.01); B29L 2031/756 (2013.01)

(58) Field of Classification Search
  CPC ....... B29C 41/12; B29C 33/68; B29C 39/006; B29C 41/38; B29C 2043/025; B01L 3/502707; B01L 2300/123; B01L 2400/086; B29L 2031/756; B29L 2031/755
  See application file for complete search history.

(56) References Cited

U.S. PATENT DOCUMENTS

| | | | |
|---|---|---|---|
| 4,702,877 A | | 10/1987 | Davis, Jr. |
| 5,487,897 A * | | 1/1996 | Polson ................ A61K 9/0024 424/426 |
| 6,123,798 A * | | 9/2000 | Gandhi ................. B07C 5/342 156/292 |
| 6,503,628 B1 | | 1/2003 | Janarthanan |
| 10,190,100 B1 * | | 1/2019 | Liu ........................ C12Q 1/006 |
| 10,730,236 B2 * | | 8/2020 | Houser ................ B29C 64/165 |
| 2002/0138049 A1 * | | 9/2002 | Allen ............... A61B 5/150022 604/272 |
| 2002/0150695 A1 * | | 10/2002 | Kodama ............. C23C 16/4405 427/534 |
| 2002/0160697 A1 * | | 10/2002 | Okamura ................ B24B 49/14 451/53 |
| 2002/0162791 A1 * | | 11/2002 | Jacobson ............. B23K 26/384 210/488 |
| 2002/0182241 A1 * | | 12/2002 | Borenstein .............. B29C 65/56 424/422 |
| 2003/0030184 A1 * | | 2/2003 | Kim ........................ C12M 41/46 264/325 |
| 2003/0047505 A1 * | | 3/2003 | Grimes ................ B01J 37/0207 210/483 |
| 2003/0064254 A1 * | | 4/2003 | Eguchi ............. H01L 21/02282 428/209 |
| 2003/0064507 A1 * | | 4/2003 | Gallagher ............... B82Y 30/00 435/287.2 |
| 2003/0219816 A1 | | 11/2003 | Solomon |
| 2004/0028875 A1 * | | 2/2004 | Van Rijn ............... B01D 67/002 428/98 |
| 2006/0154361 A1 * | | 7/2006 | Wikswo ............ B01L 3/502746 435/289.1 |
| 2006/0202385 A1 * | | 9/2006 | Xu ..................... A61M 37/0015 264/219 |
| 2006/0278580 A1 * | | 12/2006 | Striemer ............ B01D 67/0062 210/650 |
| 2008/0023890 A1 * | | 1/2008 | Sherman ................. B29C 59/18 264/650 |
| 2008/0095705 A1 * | | 4/2008 | Virtanen ............. B01F 15/0203 424/9.1 |
| 2008/0277829 A1 * | | 11/2008 | Hao ........................ B29C 33/68 264/299 |
| 2009/0029422 A1 * | | 1/2009 | Hanafusa ............... B01L 3/5027 435/91.2 |
| 2009/0076530 A1 * | | 3/2009 | Fukutomi ................ A61L 27/58 606/151 |
| 2009/0197296 A1 * | | 8/2009 | Martin .................... G01N 33/52 435/29 |
| 2009/0249950 A1 * | | 10/2009 | Koros .................... B01D 71/64 96/14 |
| 2009/0281250 A1 * | | 11/2009 | DeSimone .......... B29C 66/9534 525/418 |
| 2011/0070655 A1 * | | 3/2011 | Horiuchi ............. B01L 3/50273 436/174 |
| 2011/0215045 A1 | | 9/2011 | Zhou |
| 2012/0004621 A1 | | 1/2012 | Shaw |
| 2012/0024775 A1 * | | 2/2012 | Gong .................. B01D 67/0032 210/500.21 |
| 2012/0067433 A1 * | | 3/2012 | Friedrich .......... B01L 3/502738 137/14 |
| 2012/0230892 A1 * | | 9/2012 | Peterson ............. B01L 3/50853 422/552 |
| 2012/0244314 A1 * | | 9/2012 | Scheibner .......... B01D 39/1623 428/137 |
| 2013/0139309 A1 | | 6/2013 | Bleecher |
| 2014/0174206 A1 * | | 6/2014 | Akiyama .......... B01L 3/502707 73/863 |
| 2014/0342271 A1 | | 11/2014 | Mittelsteadt |
| 2015/0004358 A1 | | 1/2015 | Jung |
| 2015/0021829 A1 * | | 1/2015 | Nakahashi ............ B29C 43/021 264/331.11 |
| 2015/0024256 A1 * | | 1/2015 | Anandan ................ H01M 6/187 429/162 |
| 2015/0056399 A1 * | | 2/2015 | Takeoka .................. B29C 41/12 428/64.1 |
| 2015/0064300 A1 * | | 3/2015 | Wang ...................... B29C 33/42 425/405.1 |
| 2015/0073085 A1 * | | 3/2015 | Eliyahu .................... C08L 21/00 524/526 |
| 2015/0073096 A1 * | | 3/2015 | Navarro ................ C09D 153/00 525/228 |
| 2015/0091217 A1 * | | 4/2015 | Araki .................... B29C 37/0032 264/447 |

FOREIGN PATENT DOCUMENTS

| | | | | |
|---|---|---|---|---|
| CN | 101896329 A | * | 11/2010 | ........... B29C 33/505 |
| KR | 2015 0018347 A | | 2/2015 | |
| WO | WO 03/062920 A2 | | 7/2003 | |
| WO | WO 2012/166053 | | 2/2012 | |

OTHER PUBLICATIONS

CN-101896329—A translation (Year: 2023).*
Extended European Search Report for Application No. EP 167 6567 4, dated Oct. 23, 2018 (11 pages).

(56) References Cited

OTHER PUBLICATIONS

International Searching Authority, International Search Report and Written Opinion in corresponding International Application No. PCT/US2016/022680, dated Aug. 30, 2016 (15 pages).

* cited by examiner

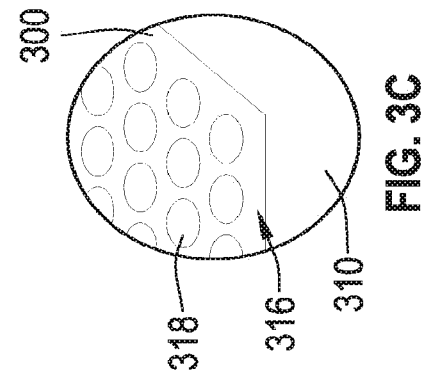
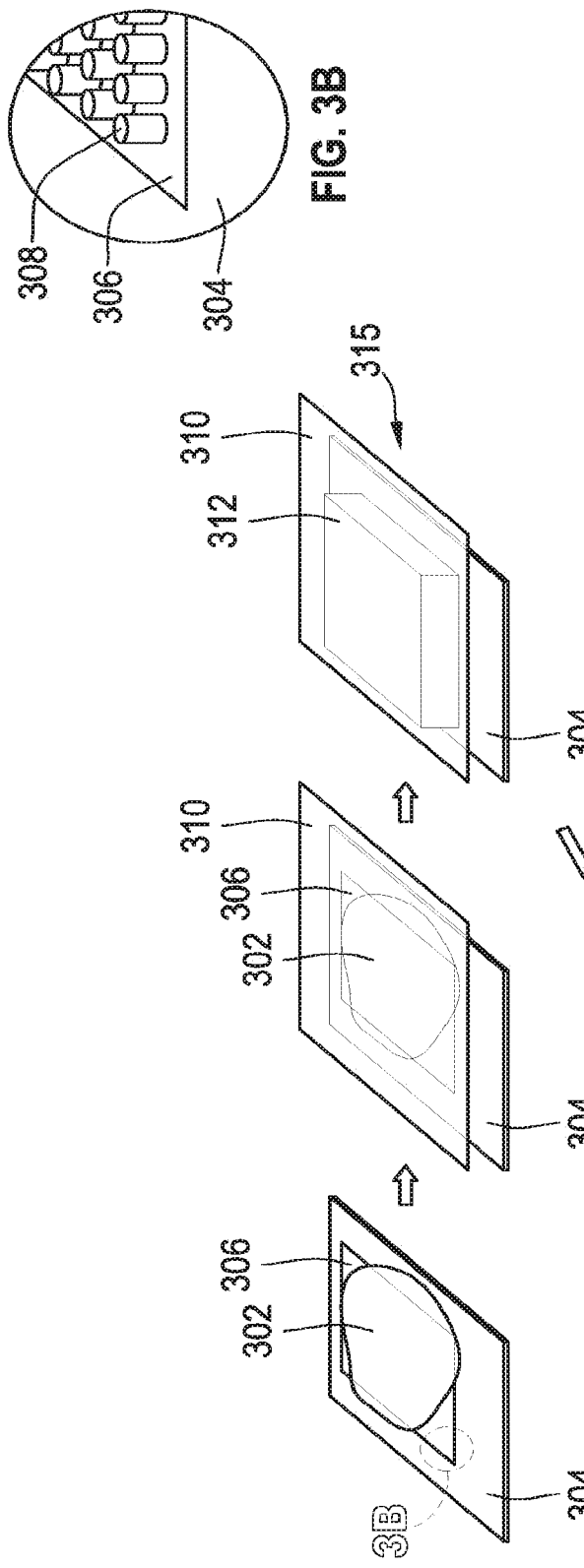
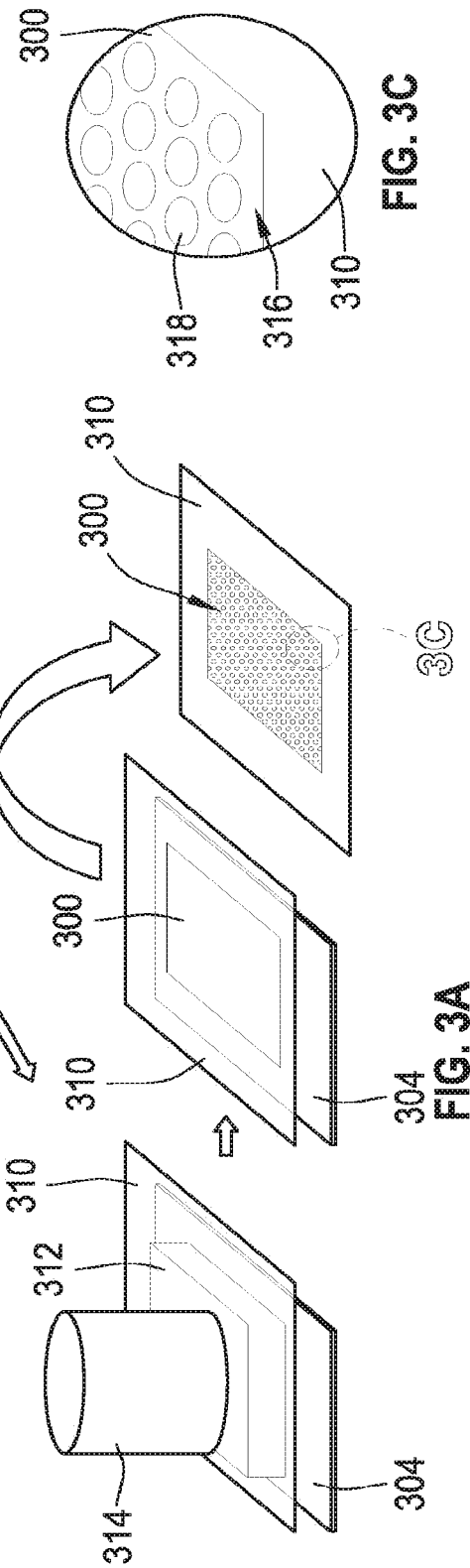

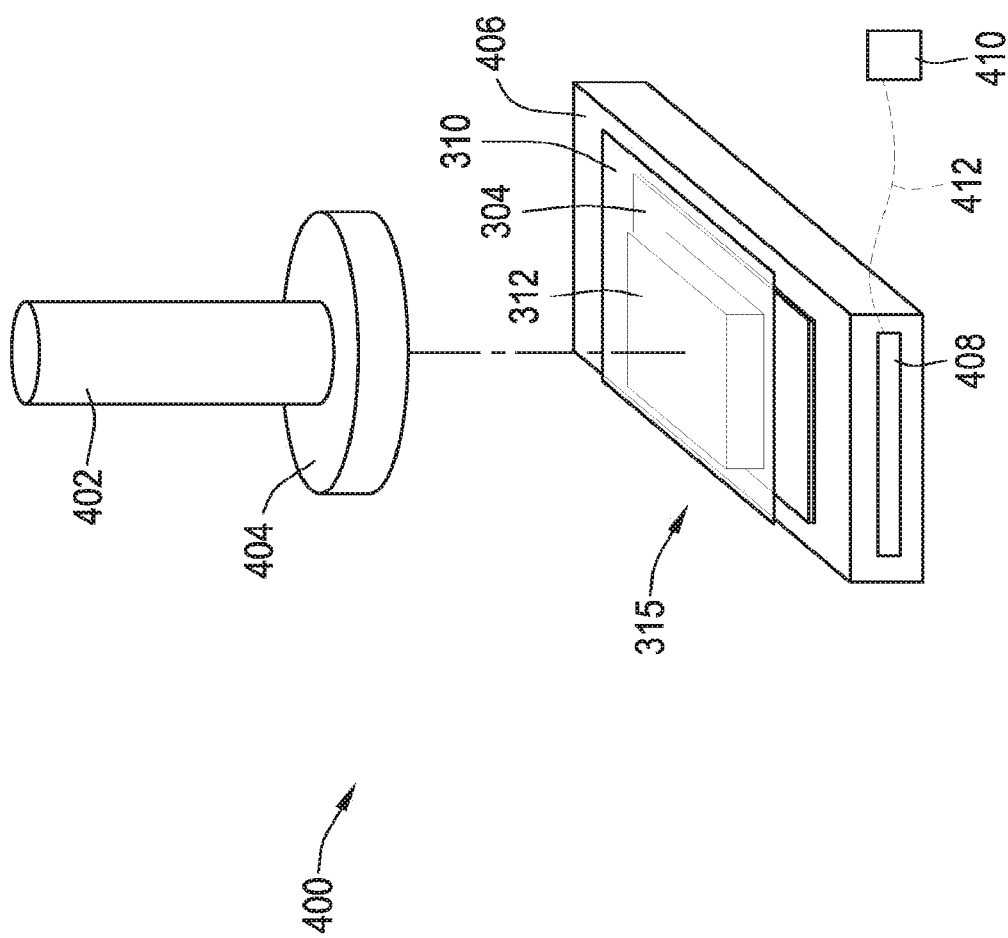

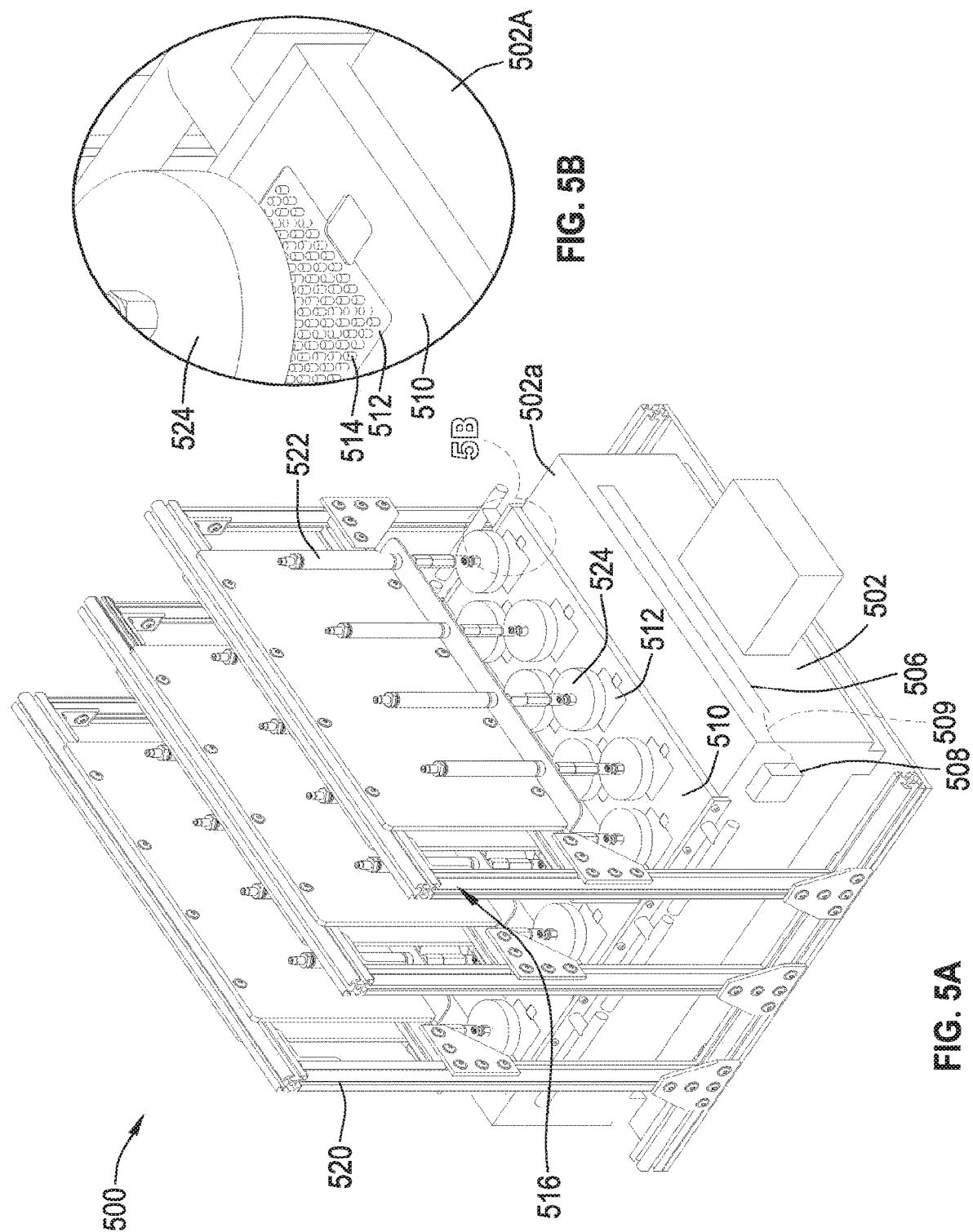

METHOD FOR MICROMOLDING A POLYMERIC MEMBRANE HAVING A PORE ARRAY

CROSS-REFERENCE TO RELATED APPLICATIONS

This application is a national stage of International Application No. PCT/US2016/022680, filed on Mar. 16, 2016, and titled "Automated Membrane Fabrication System," which claims the benefit of and priority to U.S. Provisional Patent Application No. 62/134,550, filed on Mar. 17, 2015, and titled "Automated Membrane Fabrication System," each of which is herein incorporated by reference in their respective entireties.

GOVERNMENT SUPPORT

This invention was made with government support under grant no. W911NF-12-2-0036 awarded by U.S. Department of Defense, Advanced Research Projects Agency. The government has certain rights in the invention.

FIELD OF THE INVENTION

The present invention relates generally to micro-molding of polymeric membranes and, more particularly, to forming the polymeric membranes with increased yield and reduced variability.

BACKGROUND OF THE INVENTION

Thin, porous, polymeric, and micro-molded membranes, which are made of cured polymer, such as poly-dimethylsiloxane (PDMS) are a central component of the organs-on-chip (OOC) technology and are necessary for the fabrication of OOC devices. However, present methods are not amenable to high-throughput of micro-molded membranes. By way of example, previous processes, described in more detail below, are low-yield, time-intensive processes that have high variability in the formed membranes and that require a highly-trained technical worker.

A first prior process fabricates the membranes by spin-coating uncured PDMS polymer on a chemically-treated (i.e., silane-treated) cured PDMS substrate and inverting the substrate with uncured PDMS on a mold. The uncured PDMS is, then, cured on the mold with posts on the mold forming pores in the final, cured PDMS membrane.

By way of example, referring to FIG. 1, the initial steps of the first prior process are to provide a silanized PDMS block 100 and to spin-coat a layer of PDMS 102, in which an undetermined and excessive amount of PDMS is applied, onto the PDMS block 100. Then, the spin-coated PDMS block 104 is placed onto a silicon wafer 106 with a post array 108 having a plurality of posts. To cure the spin-coated PDMS block 104, a weight 110 is placed on a glass slide 112, which is placed on top of the spin-coated PDMS block 104 and the silicon wafer 106. After the curing process is over, the spin-coated PDMS block 104 and a newly formed membrane 114 is carefully peeled off the silicon wafer 106. The membrane 114 has pores that match posts of the post array 108. This first prior process, as mentioned above, is not amenable for high-throughput fabrication of molded membranes.

A second prior process tried to improve on the spin-coating of the first prior process. The spin-coating required significant time for processing (i.e., approximately 10 minutes per membrane sample) and introduced significant sample variability. The second process modified the process to use compression molding rather than spin-coat layer molding. Instead of spin-coating each sample, the second process involved the pouring of an excess volume of uncured PDMS polymer over the post mold and compressed the mold. Compression was achieved by placing the same chemically treated (i.e., silane-treated) cured PDMS substrate on the uncured PDMS and mold, and under a weight. The PDMS, then, cures in the post mold, forming pores around the posts.

The second prior process is shown in FIG. 2. A silicon wafer 200 with a post array 202 is provided and an undetermined amount of uncured PDMS 204 is poured onto the silicon wafer 200. Then, a silanized PDMS block 206 is placed on top of the silicon wafer 200 and the poured PDMS 204. The PDMS block 206, the silicon wafer 200, and the poured PDMS 204 are cured with a weight 208 placed on top of a glass slide 210, which is placed on top of the PDMS block 206. The weight 208 requires careful selection and customization based on the arbitrary amount of PDMS 204 poured onto the silicon wafer 200. Thus, the weight 208 would typically vary on a case-by-case basis. After completing the curing process, the PDMS block 206 is peeled off the silicon wafer 200, resulting in a newly formed membrane 212 on the PDMS block 206. The membrane 212 has pores that match posts of the post array 202.

Although the second prior process reduced processing time and improved yield, it continues to fail to be amenable for high-throughput fabrication of molded membranes. Further, both prior processes involve a chemical treatment requiring a silane-based chemical modification of the surface of the cured PDMS substrate. This chemical treatment varies significantly based on environmental factors, including the relative humidity and temperature in the environment in which the chemical treatment was carried out. Additionally, the chemical treatment requires significant hands-on processing time, with each treatment taking between 1-12 hours. Furthermore, only 4-6 membrane samples' worth of substrate could be treated during each treatment.

Therefore, there is a continuing need for providing micro-membrane fabrication method and system that solves the above and other problems.

SUMMARY OF THE INVENTION

According to one aspect of the present invention, a method for micro-molding a polymeric membrane includes pouring a predetermined volume of curable polymer unto a micro-fabricated mold having a post array with a plurality of pillars, and overlaying the poured polymer with a support substrate. By way of example, the support substrate is in the form of a film, such as a thermoplastic film, a thermoset film, a molecular film, a degradable-polymer film, etc. The method further includes placing a spacer, such as a rubber spacer, in contact with the support substrate and applying a force to an exposed side of the spacer for compressing the support substrate and the polymer. While applying the force, the polymer is cured on the mold for a predetermined time period and at a predetermined temperature to a polymeric membrane having a pore array with a plurality of pores corresponding to the plurality of pillars of the post array. The polymeric membrane is removed from the support substrate.

According to another aspect of the invention, a system is directed to simultaneously micro-molding a plurality of polymeric membranes and includes a base structure with a top surface, a heating device mounted for heating the top surface of the base structure, and a controller outputting a heating signal responsive to which the heating device maintains a predetermined curing temperature for a predetermined curing time. The system further includes at least one tray having a plurality of mold-receivers, the tray being placed on the top surface of the base structure, and a plurality of molds, each of the molds being inserted in a respective one of the plurality of mold-receivers and receiving an uncured polymer that will be formed into one of the plurality of polymeric membranes. The system also includes at least one bank of force-generating devices, the bank including a supporting frame mounted adjacent to the base structure, and a plurality of force-generating devices mounted to the supporting frame. The plurality of force-generating devices are simultaneously movable to apply a predetermined force to respective ones of the plurality of molds, each of the force-generating devices including a bottom contact surface mounted proximal to the top surface of the base structure.

According to yet another aspect of the invention, a method is directed to simultaneously micro-molding a plurality of polymeric membranes and includes placing a plurality of micro-fabricated molds into a respective mold-receiver of a tray having a plurality of mold-receivers. Each of the plurality of micro-fabricated molds has a post array with a plurality of pillars. A predetermined volume of curable polymer is poured in each of the plurality of micro-fabricated molds, and the poured polymer is overlaid in each of the plurality of micro-fabricated molds with a respective support substrate. A spacer is placed in contact with each support substrate, and a force is applied, via a plurality of force-generating devices, to an exposed side of each spacer for compressing the support substrate and the poured polymer in each of the plurality of micro-fabricated molds. While applying the force, the poured polymer in each of the plurality of micro-fabricated molds is cured on a heating device for a predetermined time period and at a predetermined temperature to form a plurality of polymeric membranes having a pore array with a plurality of pores corresponding to the plurality of pillars of the post array. Each of the plurality of polymeric membrane is removed from the respective mold of the plurality of micro-fabricated molds.

According to yet another aspect of the invention, a method is directed to forming a polymeric membrane on a substrate carrier and include pouring a predetermined volume of curable polymer unto a micro-fabricated mold having an array of pillars. A support substrate is placed over the poured polymer and a spacer is placed in contact with the support substrate. While a force is applied to the spacer, the polymer is cured in the mold to form a polymeric membrane having a pore array corresponding to the array of pillars. The polymeric membrane is removed from the mold.

According to yet another aspect of the invention, a membrane and substrate molded assembly includes a support substrate and a polymeric membrane that is formed from a predetermined volume of polymer poured onto a mold with a pillar array. The polymeric membrane is removably formed on the support substrate while cured under a compressive weight. The polymeric membrane has a pore array corresponding to the pillar array of the mold.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3A is a diagrammatic illustrating a method of forming a membrane in accordance with one embodiment of the present invention.

FIG. 3B is an enlarged view illustrating pillars of a mold post array.

FIG. 3C is an enlarged view illustrating pores of a membrane pore array.

FIG. 4 is a perspective view illustrating a single-mold apparatus in accordance with another embodiment of the present invention.

FIG. 5A is a perspective view of a membrane fabrication machine in accordance with another embodiment of the present invention.

FIG. 5B is an enlarged view illustrating a mold inserted in a respective mold-receiver of the membrane fabrication machine of FIG. 5A.

Figure 1:
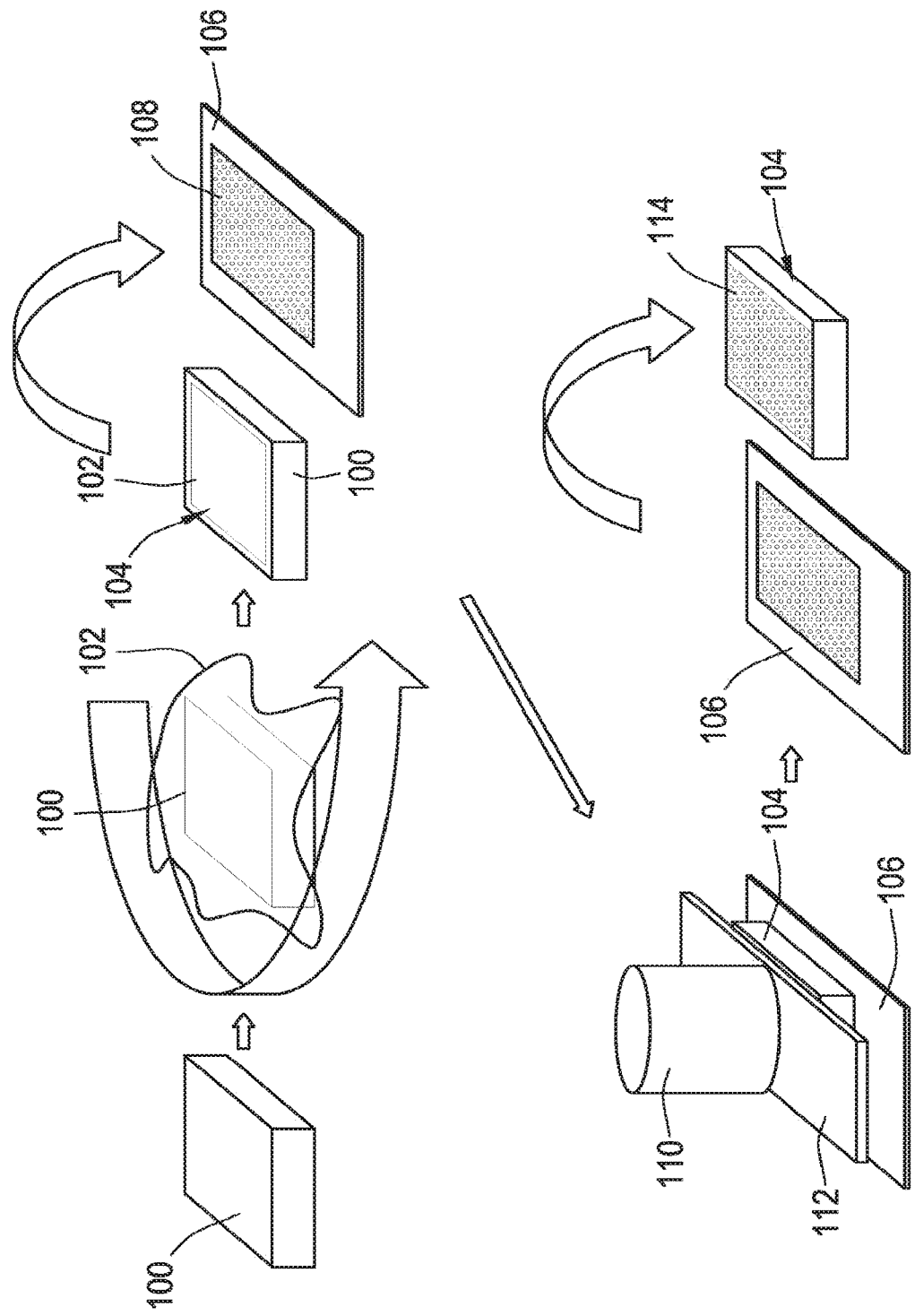
FIG. 1 is a diagrammatic illustrating a previous problematic method of forming a membrane in accordance with a first process.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to FIGS. 3A-3C, a method of micro-molding a thin, polymeric membrane 300 provides several advantages relative to previous methods, including the two methods described above in reference to FIGS. 1 and 2. For example, the method reduces hand-on time, drastically increases yield, significantly reduces variability, and eliminates skill-based processes that require special training. By way of a specific example, the method eliminates chemical treatment of a carrier substrate (e.g., spin-coating of PDMS layer 102 in FIG. 1) by changing to a new material. This, and other improvements necessitated by the change in material, are described in more detail below.

To form a porous membrane 300, the method includes pouring a predetermined (or fixed) volume of curable polymer 302 unto a micro-fabricated mold 304 having a post array 306 with a plurality of pillars 308. According to some embodiments, the pillars 308 have a circular diameter that is in the range of approximately 0.001 millimeters to 0.5 millimeters. In alternative embodiments, the post array 306 includes one or more geometric shapes, including hexagons, pentagons, squares, triangles, or other polygons. The polymer 302 is optionally a Poly Dimethyl Siloxane (PDMS)

polymer and the mold 304 is a silicon wafer. The poured polymer 302 is overlaid with a carrier substrate 310, which according to one example is in the form of a thermoplastic film (e.g., a polycarbonate film). In alternative embodiments, the polycarbonate film is replaced with a polyester material, e.g., a polyethylene terephthalate (PET) material, a polyurethane material, a degradable material, and/or a material that can be dissolved when placed into another solvent (e.g., plastics that dissolve in acetone). Some examples of the degradable material include polylactic acid, polyglycolic acid, poly(lactic-co-glycolic acid), and/or biological polymer film (e.g., chitosan or collagen). In yet other alternative embodiments, the polycarbonate film is formed and, after the porous membrane 300 is formed, dissolved or degraded away from the porous membrane 300 (instead of having to lift the polycarbonate film off away from the porous membrane 300). By way of a further example, and if so desired, biopolymer films are left on the porous membrane 300 and are used for cell culture.

The carrier substrate 310 is selected to be a substrate carrier of the polymeric membrane 300 such that chemical treatment is no longer required. Because the chemical treatment of previous carrier substrates, such as the PDMS block 100 in FIG. 1 or the silanized PDMS bock 206 in FIG. 2, introduced high variability in the formed membranes, the present method relies on the carrier substrate 310 that does not require chemical treatment. Polycarbonate film was selected as one option for the carrier substrate 310 based on its plasma-tunable adhesion properties and its advantageous mechanical properties. For example, polycarbonate film is flexible, lightweight, and tear-resistant. The plasma tuning of the polycarbonate film alters its tackiness to a point that permits an appropriate level of adhesion to the membrane 300.

A spacer 312, such as a rubber spacer, is placed in contact with the carrier substrate 310, without making contact with the uncured polymer 302. The rubber spacer 312 is optionally made from a PDMS polymer, similar to the curable polymer 302, and helps to evenly distribute the force. Then, a weight 314 is placed on the rubber spacer 312 to compress the carrier substrate 310 together with the uncured polymer 302. Thus, a force is applied by the weight 314 to an exposed side of the rubber spacer 312 to achieve the compression between the carrier substrate 310 and the uncured polymer 302. While the weight is on the rubber spacer 312, the uncured polymer 302 is cured on the micro-fabricated mold 304 for a predetermined time period and at a predetermined temperature. For ease of understanding, the uncured polymer 302, the mold 304, the carrier substrate 310, and the rubber spacer 312 are also referred to as the mold assembly 315.

According to optional embodiments, the curing of the uncured polymer 302 is achieved in part via one or more of a hot plate, an oven chamber, a compressive element placed in an oven, a thermoelectric device, a geothermal device, a frictional heat dissipation device, and a solar heat device. Thus, instead of or in addition to heating, the curing is optionally activated via catalysis and or electromagnetic radiation (including ultraviolet light radiation).

In response to completing the curing process, the polymeric membrane 300 is formed on the carrier substrate 310 from the (now) cured polymer 302. The polymeric membrane 300 and the support carrier 310 are removably adhered to each other. The polymeric membrane 300 has a pore array 316 with a plurality of pores 318 corresponding to the plurality of pillars 308 of the post array 306. The polymeric membrane 300 can later be peeled-off from the carrier substrate 310. According to an example, the polymeric membrane 300 has a thickness that is less than approximately 1 millimeter, such as 30, 50, or 100 microns. In other embodiments, the carrier substrate 310 can be dissolved or degraded to release the polymeric membrane 300. In yet other embodiments, the polymeric membrane 300 is formed as a multi-layer membrane in which the layers consist of different materials, with each layer having molded structures.

One benefit of integrating the carrier substrate 310 and the rubber spacer 312 is that variability in forming polymeric membranes 300 is greatly reduced, resulting in improved consistency between the formed polymeric membranes 300. Other benefits include a reduction of hands-on time for forming the polymeric membrane 300 and an increase yield of useful membranes 300.

Figure 2:
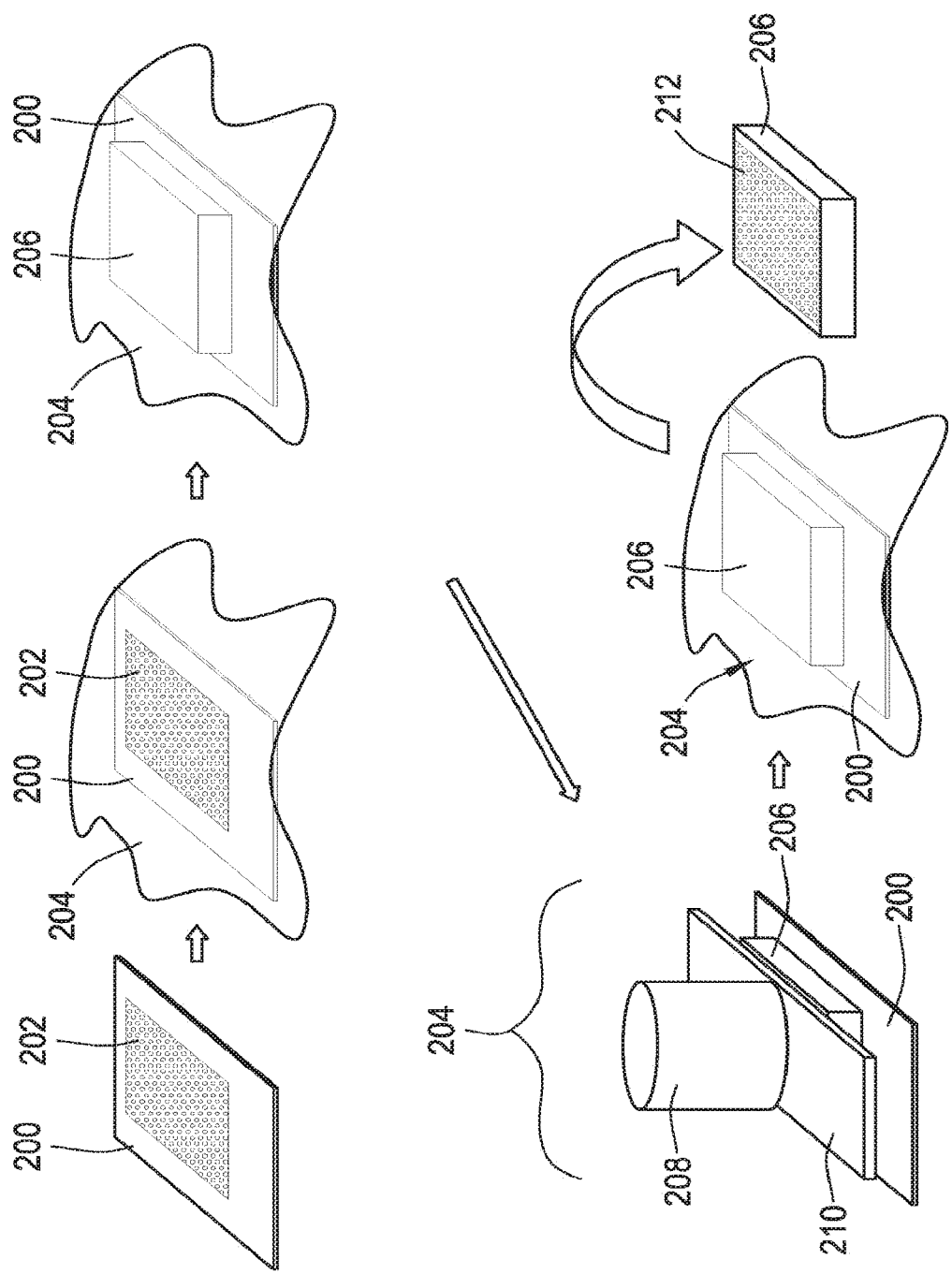
FIG. 2 is a diagrammatic illustrating another previous problematic method of forming a membrane in accordance with a second process.

For example, one reason for reducing the hands-on time is directed to the requirement in previous methods to carefully select a compression weight that would avoid an undue force being applied to the spin-coated layer 102 (FIG. 1) or the poured PDMS 204 (FIG. 2). In contrast to the compression weight of previous methods, e.g., the weight 110 (FIG. 1) and the weight 208 (FIG. 2), the present compression weight is now easily increased to higher forces, such as 1500 grams. In other words, the present method is less sensitive to the applied force and, as such, a fabricator does not have to be concerned with applying too much weight during the curing process. In turn, less time and less training is required for fabricating the polymeric membrane 300. By way of example, the applied force is in the range of about 1 kilogram to about 10 kilograms.

Additionally, in contrast to previous methods, the weight in the present process is a constant weight that does not require customization on a case-by-case basis. As discussed in more detail below, in alternative embodiments the force is generated and applied via one or more of an electromagnetic device, a magnetic device, a hydraulic device, a pneumatic device, and a mechanical device.

In another example, a reason for improving consistency in the formed polymeric membranes 300 is directed to pouring a predetermined volume of curable polymer 302, instead of pouring an arbitrary amount of PDMS as in previous methods. Pouring an arbitrary volume of PDMS resulted in membranes with significantly different geometric configurations, while pouring a predetermined volume achieves membranes with consistent and uniform geometric configurations.

Referring to FIG. 4, a single-mold apparatus 400 for forming the polymeric membrane 300 includes an air cylinder 402, a disk 404, and a hot plate 406. The air cylinder 402 generates a force that is applied to the rubber spacer 312, which compresses the substrate 310 against the mold 304. Specifically, the air cylinder 402 is slowly ramped to a defined air pressure, applying a compressive force to the mold assembly 315, with the disk 404 being pressed in direct contact with the rubber spacer 312. According to one example, the disk 404 is an aluminum disk attached to the air cylinder 402 and separate from the rubber spacer 312. According to another example, the disk 404 and the rubber spacer 312 are integrated as a single component.

The hot plate 406 includes a heating element 408 that is started and controlled by a proportional-integral-derivative (PID) controller 410. The heating element 408, responsive to a signal 412 received from the controller 410, generates heat for a predetermined time and at a predetermined temperature. For example, the heat is generated in accordance with a ramped-up temperature profile that slowly heats up the mold assembly 315, e.g., a low temperature during a first time period, a high temperature during a second time period, a higher temperature during a third time period, etc. The ramped-up temperature profile allows, for example, air molecules trapped between the carrier substrate 310 and the uncured polymer 302 to escape. If a sudden, high temperature was applied (as in previous methods), the air molecules would be trapped between the carrier substrate 310 and the uncured polymer 302, with the resulting polymeric membrane 300 being of poor/undesired quality.

The above example refers to an air cylinder, which is beneficial because pneumatic compression is tunable, enabling a wide range of compressive force. Optionally, the pneumatics associated with the air cylinder are controlled with solenoids and/or valves. However, in other embodiments, the force generation is not limited to pneumatic devices. For example, instead of or in addition to an air cylinder, the force generation is optionally achieved via electromagnetic devices (e.g., motors, actuators, solenoids, etc.), magnetic devices, hydraulic devices, and/or mechanical devices (e.g., springs, gears, etc.).

Referring to FIGS. 5A and 5B, a system 500 is directed to simultaneously micro-molding a plurality of polymeric membranes, such as the polymeric membrane 300 described above. The system 500 includes a base structure 502 having a top surface 502a, and a heating device 506 mounted for heating the top surface 502a of the base structure 502. The heating device 506 is communicatively coupled to a controller 508, which outputs a heating signal 509 responsive to which the heating device 506 maintains a predetermined curing temperature for a predetermined curing time. Although a typical material for some or all components of the system 500 is aluminum, other materials include steel, high-performance plastics, other metals, ceramics, carbon fiber, bamboo, natural materials, and/or brick materials.

The controller 508 is integrated with or separate from the base structure 502 or other components of the system 500. By way of example, the controller 508 is a separate, independent component. In other embodiments, the controller 508 is replaced with manual adjustments. In other words, instead of using a controller 508 to determine control inputs/outputs, manual adjustments are provided (e.g., switches/buttons manually actuated by a user, an analog device for heat control, etc.).

The system 500 further includes at least one tray 510 having a plurality of mold-receivers 512. The tray 512 is placed on the top surface 502a of the base structure 502. A plurality of molds 514 are inserted, respectively, in the mold-receivers 512. Different molds having different sized and shaped posts can be inserted into the tray 514 such that the system 500 can produce membranes 300 with pores having various sizes and shapes.

The system 500 also includes multiple banks 516 of force-generating devices, with each bank 516 including a supporting frame 520 and a plurality of force-generating devices 522. The supporting frame 520 is mounted adjacent to the base structure 502. The force-generating devices 522 are mounted to the supporting frame 520 and are simultaneously movable to apply a predetermined force to respective ones of the plurality of molds 514.

By way of example, each of the force-generating devices 522 is an air cylinder such as the air cylinder 402 illustrated in FIG. 4. In this example, each of the force-generating devices further includes a disk 524 with a bottom contact surface mounted proximal to the top surface 502a of the base structure 502. Additionally, according to this example, the system 500 includes 24 single-mold setups such as the single-mold apparatus 400 of FIG. 4 (e.g., 3 banks 516 with 8 single-mold setups per bank). In other examples, the system 500 is configured to have different numbers of banks 516 and/or single-mold setups 400.

The system 500 provides the benefit of automating the process of forming polymeric membranes, which helps significantly reduce hands-on process time, eliminates skill-based steps in the process, reduces variability, and increases yield. For example, automation of compression, curing, and/or heating eliminated the most time-consuming process steps and all of the skill-based steps required in previous methods.

Additionally, the system 500 reduces variability by using a PID-controlled heating element and pneumatic compression. The PID-controlled heating element provides temporal control of the temperature via PID control and an even-heating hotplate provides spatial consistency of hotplate temperature. The pneumatic compression provides consistent application of a compressive force to the mold assembly Finally, the system 500 increases overall process yield by use of greater compressive force (e.g., approximately six times greater than in previous methods) to generate a higher area of a patterned membrane, and eliminates curing variability by using a PID-controlled heating recipe. The heating recipe allows the user to tune the curing steps are required to any desirable recipe. Furthermore, the automation of the process has enabled high-throughput fabrication of micro-molded membranes, with throughout increasing, for example, more than tenfold. Consequently, overall chip fabrication throughput (e.g., chips for use in 00C devices) has also increased.

Figure 6:
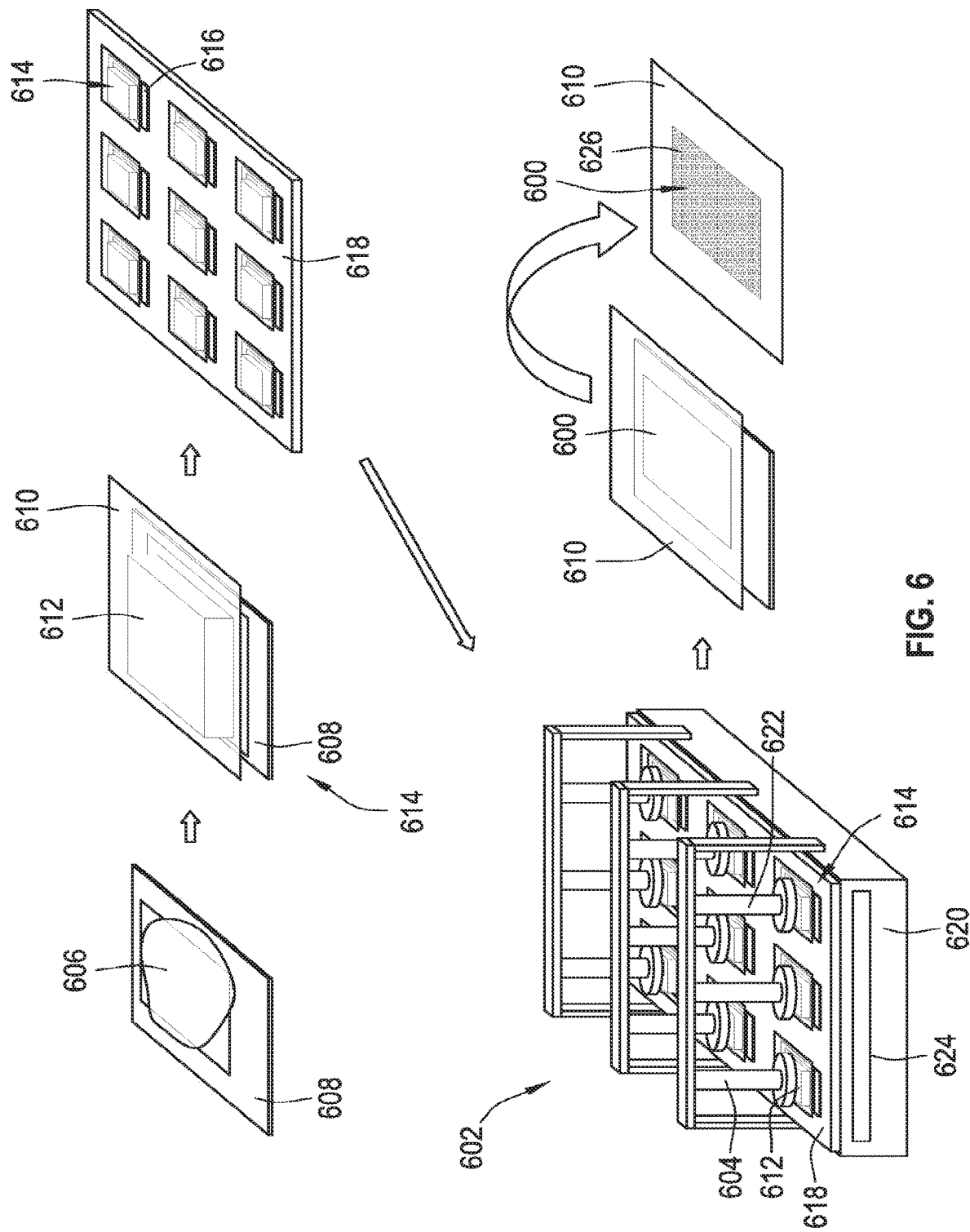
FIG. 6 is a diagram illustrating a method of fabricating membranes with the fabrication machine of FIG. 5A.

Referring to FIG. 6, a method is directed to simultaneously micro-molding a plurality of polymeric membranes 600 by using a system 602 having nine single-mold setups 604. Initially, a predetermined volume of curable PDMS polymer 606 is poured in a micro-fabricated mold 608. The mold 608 is generally similar to identical to the molds described above (e.g., includes a post array with a plurality of pillars). A poly-carbonate support substrate 610 is overlaid on top of the PDMS polymer 606 and a spacer 612, such as a rubber spacer, is placed on top of and in contact with the support substrate 610. The PDMS polymer 606, the mold 608, the support substrate 610, and the rubber spacer 612 form generally a mold assembly 614 that is placed in a respective mold-receiver 616 of a tray 618.

The tray 618 includes nine distinct mold-receivers 616. Thus, in this example, the process of forming the mold assembly 614 is repeated eight more times to form the total of nine mold assemblies 614, one for each mold-receiver 616 of the tray 618. After inserting the mold assemblies 614, respectively, in the mold-receivers 616, the tray 618 is placed on a base structure 620 of the system 602.

A simultaneous force is applied, via a plurality of force-generating devices 622, to an exposed side of each rubber spacer 612 for compressing the support substrate 610 and the PDMS polymer 606 in each of the micro-fabricated molds 608. While applying the force, the support substrate 610 and the poured PDMS polymer 606 of each micro-fabricated mold 608 are cured by a heating device 624 for a predetermined time period (e.g., 4 hours or more) and at a predetermined temperature (e.g., 60 degrees Celsius or higher). According to one example, and in reference to PDMS being the membrane material, a temperature range is approximately 60-80 degrees Celsius. According to other examples, temperatures less than approximately 60 degrees Celsius and up to approximately 200 degrees Celsius are also acceptable. The heating device 624 is one or more of a plurality of different devices. For example, the heating device 624 is a hot plate, an oven-like chamber, a thermoelectric device, a geothermal device, a frictional heat dissipation device, and/or a solar heating device.

In response to completing the curing, the plurality of polymeric membranes 600 is formed generally simultaneously from respective samples of uncured polymers 606. Each of the polymeric membranes 600 is adhered to the support substrate 610 and the membranes 600 can be peeled from the substrate 610. Each of the polymeric membranes 600 has a pore array 626 with pores matching pillars of a post array of the respective mold 608 (e.g., similar to pillars 308 of mold 304 illustrated in FIGS. 3A and 3B).

According to alternative embodiments, other features are implemented instead of or in addition to the features discussed above. For example, instead of applying a single force to a mold assembly, e.g., a single air cylinder 402 applying a single force to mold assembly 315, the force to mold assembly ratio can vary. By way of example, a plurality of air cylinders (e.g., two air cylinders) generate the force required for a single mold assembly 315. Or, in another example, a single air cylinder generates the force required for a plurality of mold assemblies 315 (e.g., two mold assemblies 315).

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A method for micro-molding a porous polymeric membrane having a pore array that contains a plurality of pores, the method comprising:
   introducing a predetermined volume of polymer into a micro-fabricated mold having a post array with a plurality of pillars, each pillar having a top surface;
   overlaying the polymer with a support substrate, the support substrate being in the form of a film;
   applying a force for compressing the support substrate and the polymer, the support substrate being in contact with the top surface of the plurality of pillars;
   while applying the force, curing the polymer on the mold for a predetermined time period and at a predetermined temperature to form a polymeric membrane having a pore array with a plurality of pores corresponding to the top surface of each of the plurality of pillars of the post array;
   removing the support substrate from the mold with the polymeric membrane adhered to the support substrate, said removing comprises peeling the membrane from the substrate after the curing process is over, resulting in a newly formed porous membrane, wherein the porous polymeric membrane has a pore array with a plurality of pores corresponding to said plurality of said post array.

2. The method of claim 1, wherein the film is selected from the group consisting of a thermoplastic film, a thermoset film, a molecular film, and a degradable-polymer film.

3. The method of claim 1, wherein the film includes a polycarbonate material.

4. The method of claim 1, wherein the force is generated via one or more of an electromagnetic device, a magnetic device, a hydraulic device, a pneumatic device, and a mechanical device.

5. The method of claim 1, wherein the curing is achieved in part via one or more of a heated plate, an oven chamber, a compressive element placed in an oven, a thermoelectric device, a geothermal device, a frictional heat dissipation device, and a solar heat device.

6. The method of claim 1, wherein the film includes a material selected from the group consisting of a polyester material, a polyurethane material, a degradable material, and a material that can be dissolved when placed into a solvent.

7. The method of claim 6, wherein the material that can be dissolved when placed into a solvent is a plastic that can dissolve in acetone.

8. The method of claim 6, wherein the degradable material is selected from the group consisting of polylactic acid, polyglycolic acid, poly(lactic-co-glycolic acid), and a biological polymer film.

9. The method of claim 8, wherein the biological polymer film is selected from the group consisting of chitosan and collagen.

10. The method of claim 1, wherein the film is a biological polymer film.

11. A method for micro-molding a porous polymeric membrane having a pore array that contains a plurality of pores, the method comprising:
    introducing a volume of polymer into a micro-fabricated mold having a post array with a plurality of pillars, each pillar having a top surface;
    overlaying the polymer with a support substrate, the support substrate being in the form of a film;
    placing a spacer having a first side and a second side, the first side being in contact with the support substrate;
    applying a force for compressing the support substrate and the polymer such that the force is applied to the second side of the spacer, the second side being exposed, and being opposite the first side;
    while applying the force, curing the polymer on the mold for a predetermined time period of greater than 4 hours and at a predetermined temperature of 60 degrees Celsius or higher to form a porous polymeric membrane having a pore array with a plurality of pores corresponding to the top surface of each of the plurality of pillars of the post array; and
    removing the support substrate from the mold with the porous polymeric membrane adhered to the support substrate.

12. The method of claim 11, wherein the spacer is a rubber spacer and at least one of the polymer and the rubber spacer contains Poly Dimethyl Siloxane (PDMS).

13. The method of claim 11, wherein the force is applied to compress the spacer, the force having an associated mass that is in the range of about 1 kilogram to about 10 kilograms.

* * * * *